(12) United States Patent
Kaylor et al.

(10) Patent No.: US 7,098,040 B2
(45) Date of Patent: Aug. 29, 2006

(54) SELF-CONTAINED SWAB-BASED DIAGNOSTIC SYSTEMS

(75) Inventors: Rosann Marie Matthews Kaylor, Cumming, GA (US); RameshBabu Boga, Roswell, GA (US); Kaiyuan Yang, Cumming, GA (US); David Samuel Cohen, Alpharetta, GA (US); Herb Velazquez, Neenah, WI (US); Amanda Lee O'Connor, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 183 days.

(21) Appl. No.: 10/744,235

(22) Filed: Dec. 23, 2003

(65) Prior Publication Data
US 2005/0136553 A1 Jun. 23, 2005

(51) Int. Cl.
*G01N 33/558* (2006.01)

(52) U.S. Cl. .............................. 436/514; 604/1; 604/3; 422/50; 422/55; 422/56; 422/57; 422/58; 422/61; 422/101; 435/287.1; 435/287.2; 435/288.1; 435/810; 435/970; 436/63; 436/518; 436/805; 436/810

(58) Field of Classification Search ............ 604/1, 604/3; 422/50, 55, 56, 57, 58, 61, 101; 435/287.1, 287.2, 288.1, 810, 970; 436/514, 436/518, 805, 810, 63
See application file for complete search history.

(56) References Cited

U.S. PATENT DOCUMENTS

| | | |
|---|---|---|
| 3,792,699 A | 2/1974 | Tobin et al. |
| 4,168,146 A | 9/1979 | Grubb et al. |
| 4,235,601 A | 11/1980 | Deutsch et al. |
| 4,366,241 A | 12/1982 | Tom et al. |
| 4,442,204 A | 4/1984 | Greenquist et al. |
| 4,447,526 A | 5/1984 | Rupchock et al. |
| 4,458,020 A | 7/1984 | Bohn et al. |
| 4,707,450 A | 11/1987 | Nason |
| 4,831,840 A | 5/1989 | Fletcher |
| 4,952,204 A | 8/1990 | Korteweg |
| 5,084,245 A | 1/1992 | Berke et al. |
| 5,129,402 A | 7/1992 | Koll et al. |
| 5,137,808 A | 8/1992 | Ullman et al. |

(Continued)

FOREIGN PATENT DOCUMENTS

EP 0354704 A1 2/1990

(Continued)

OTHER PUBLICATIONS

Search Report and Written Opinion for PCT/US2004/025860.

(Continued)

*Primary Examiner*—Christopher L. Chin
(74) *Attorney, Agent, or Firm*—Dority & Manning, PA

(57) ABSTRACT

A diagnostic test unit is provided. The test unit comprises a stem having a first end and a second end, the stem defining at least one flow channel extending between the first end and the second end. A swab is disposed at the first end of the stem, the swab being configured to collect a test sample derived from a biological source that is suspected of containing an analyte. The test unit also comprises a fluid chamber configured to contain a fluid, wherein the fluid chamber is in fluid communication with the swab via the flow channel. The test unit also comprises a rupturable seal that inhibits leakage of the fluid from the fluid chamber prior to use, and an assay for detecting the presence or absence of the analyte. The assay is in fluid communication with the swab, the flow channel, and the fluid chamber.

46 Claims, 5 Drawing Sheets

U.S. PATENT DOCUMENTS

| | | | |
|---|---|---|---|
| 5,208,535 | A | 5/1993 | Nakayama et al. |
| 5,238,649 | A | 8/1993 | Nason |
| 5,250,412 | A | 10/1993 | Giegel |
| 5,266,266 | A | 11/1993 | Nason |
| 5,278,075 | A | 1/1994 | Stone |
| 5,295,952 | A | 3/1994 | Pietrafitta |
| 5,330,917 | A | 7/1994 | Stone |
| 5,364,792 | A | 11/1994 | Stone |
| 5,395,754 | A | 3/1995 | Lambotte et al. |
| 5,449,071 | A | 9/1995 | Levy |
| 5,449,494 | A | 9/1995 | Seeney |
| 5,508,171 | A | 4/1996 | Walling et al. |
| 5,534,132 | A | 7/1996 | Vreeke et al. |
| 5,550,061 | A | 8/1996 | Stone |
| 5,660,990 | A | 8/1997 | Rao et al. |
| 5,670,381 | A | 9/1997 | Jou et al. |
| 5,869,003 | A | 2/1999 | Nason |
| 5,879,635 | A | 3/1999 | Nason |
| 5,917,592 | A | 6/1999 | Skiffington |
| 5,965,453 | A | 10/1999 | Skiffington et al. |
| 5,983,438 | A | 11/1999 | Bostick et al. |
| 6,043,047 | A | 3/2000 | Foote et al. |
| 6,194,220 | B1 | 2/2001 | Malick et al. |
| 6,197,254 | B1 | 3/2001 | Silver et al. |
| 6,241,863 | B1 | 6/2001 | Monbouquette |
| 6,248,294 | B1 | 6/2001 | Nason |
| 6,270,637 | B1 | 8/2001 | Crismore et al. |
| 6,281,006 | B1 | 8/2001 | Heller et al. |
| 6,309,818 | B1 | 10/2001 | Malinda et al. |
| 6,352,863 | B1 | 3/2002 | Guirguis |
| 6,406,451 | B1 | 6/2002 | Rowe |
| 6,436,651 | B1 | 8/2002 | Everhart et al. |
| 6,461,496 | B1 | 10/2002 | Feldman et al. |
| 6,524,530 | B1 | 2/2003 | Igarashi et al. |
| 6,541,194 | B1 | 4/2003 | DiCesare |
| 6,548,018 | B1 | 4/2003 | DiCesare et al. |
| 6,565,808 | B1 | 5/2003 | Hudak et al. |
| 6,613,576 | B1 | 9/2003 | Rodacy et al. |
| 2003/0119202 | A1 | 6/2003 | Kaylor et al. |

FOREIGN PATENT DOCUMENTS

| | | |
|---|---|---|
| EP | 1234871 A1 | 8/2002 |
| WO | WO 9525948 A1 | 9/1995 |
| WO | WO 9614570 A1 | 5/1996 |
| WO | WO 97032091 A1 | 1/1997 |
| WO | WO 9723596 A1 | 7/1997 |
| WO | WO 9827196 A1 | 6/1998 |

OTHER PUBLICATIONS

U.S. Appl. No. 10/744,607, filed Dec. 23, 2003, Lyng, et al., Swab-Based Diagnostic Systems.

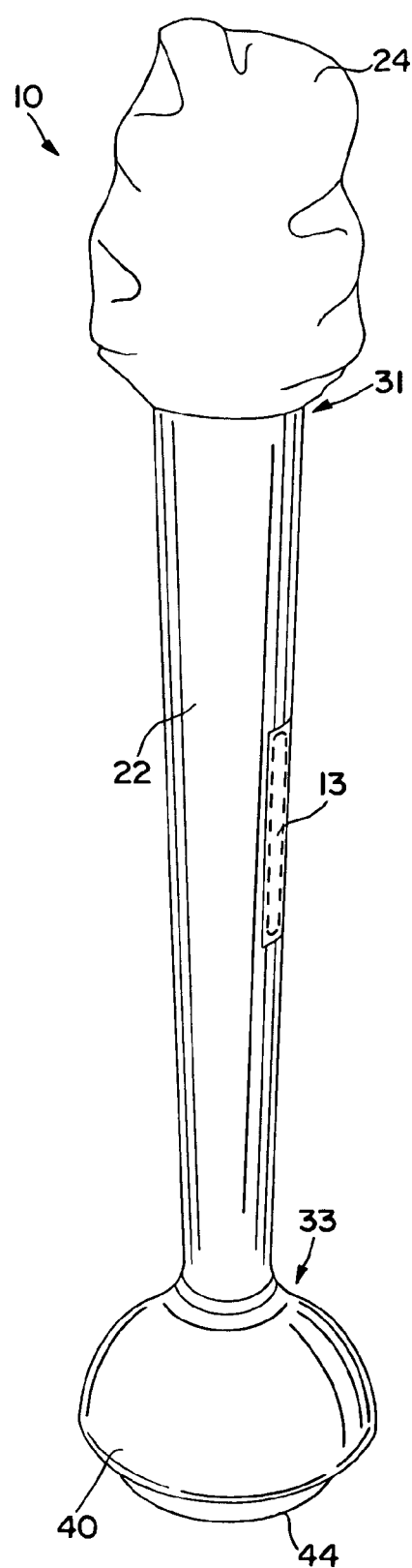
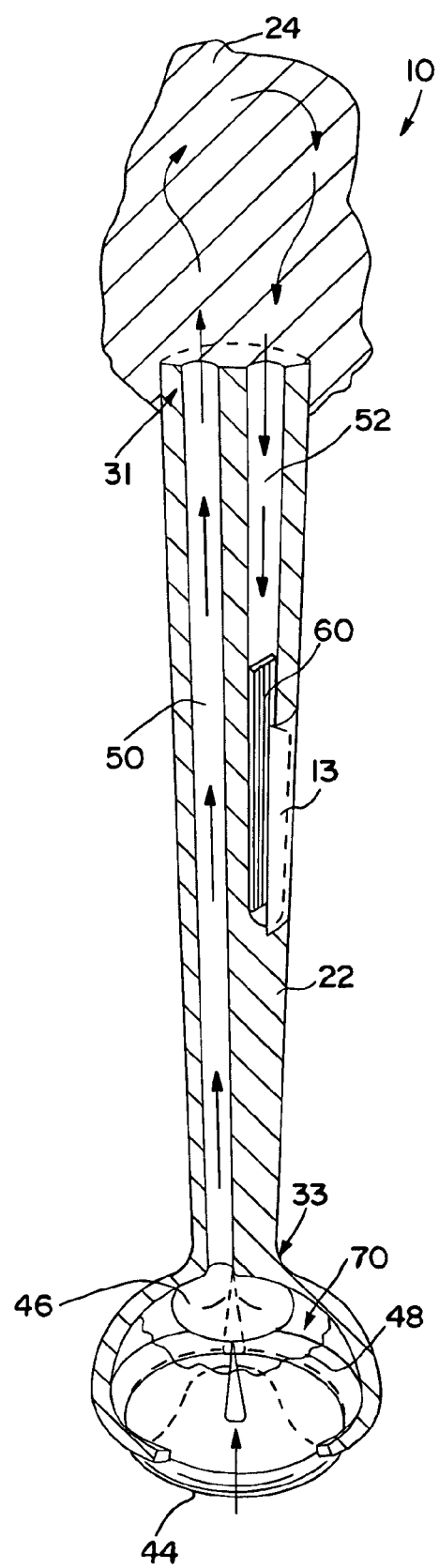
FIG. 1A
FIG. 1B

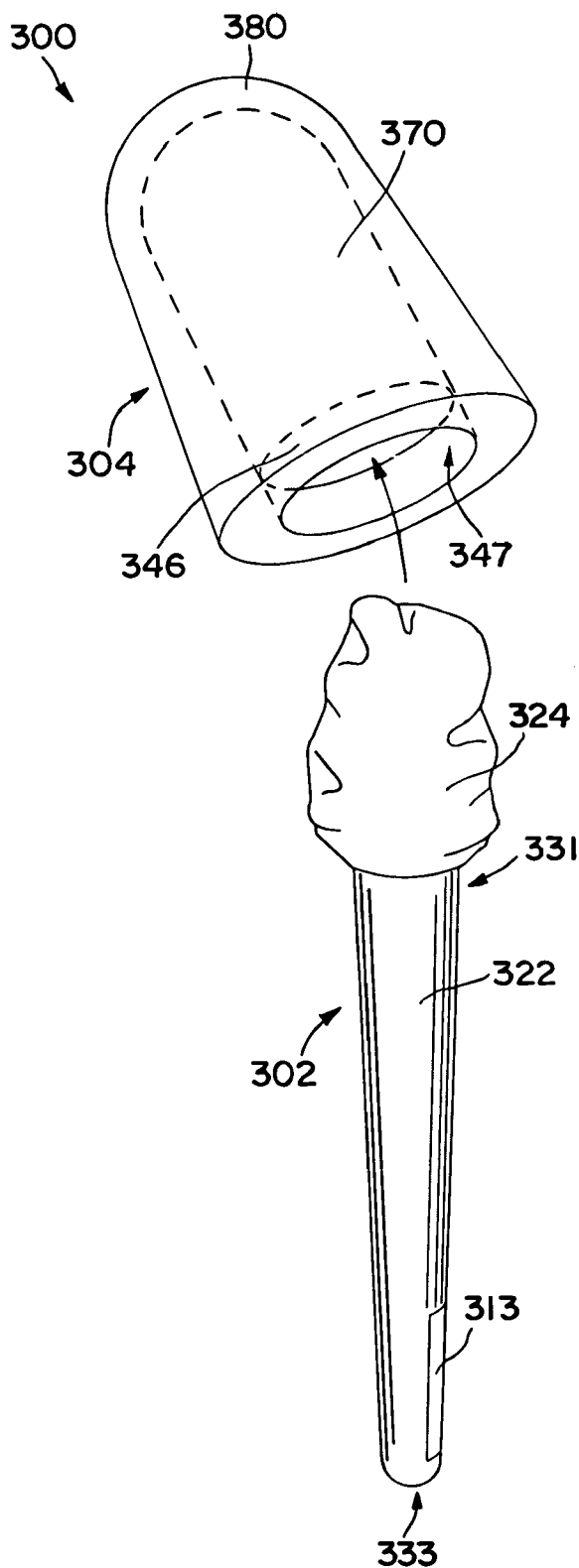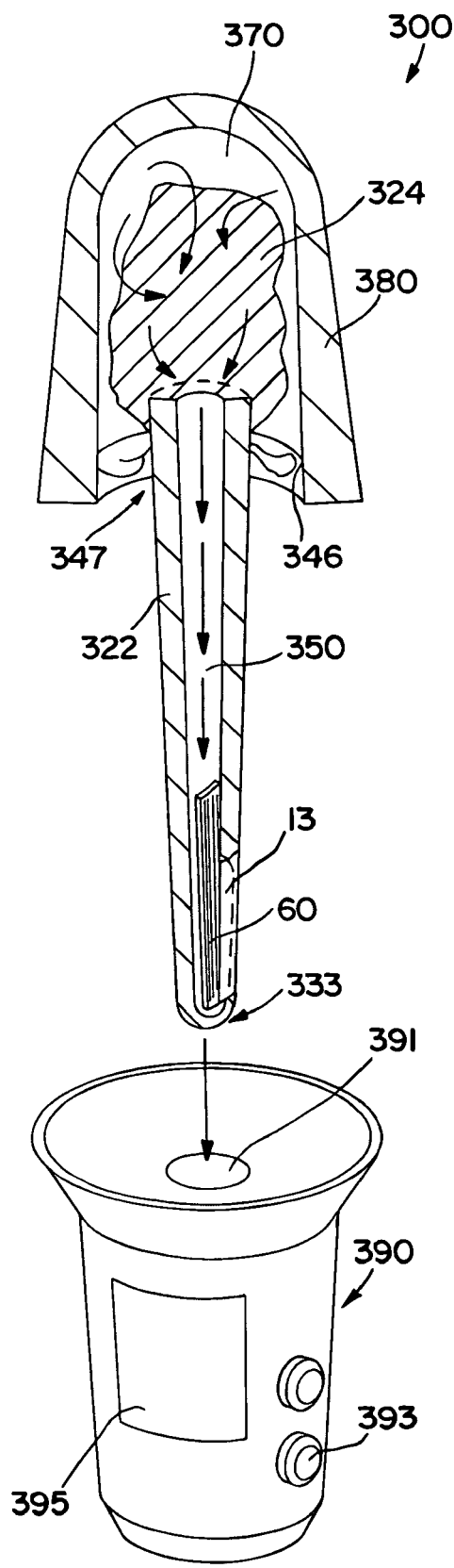
FIG. 4A
FIG. 4B

SELF-CONTAINED SWAB-BASED DIAGNOSTIC SYSTEMS

BACKGROUND OF THE INVENTION

Medical swabs are commonly used to collect biological specimens from patients. Such medical swabs generally include a fibrous tip at one end of an elongated stick or stem. Once a sample is collected, it may be transferred from the tip to a testing medium for performance of an assay to determine the presence or absence of an analyte of interest. Some systems, known as "all-in-one" swab systems, have been developed that provide both the reagents for the immunoassay and the swab in a single, self-contained apparatus. For example, U.S. Pat. No. 6,248,294 to Nason describes a substantially self-contained diagnostic test unit for collecting and analyzing a biological specimen. The test unit has a tubular housing defining a specimen chamber for receiving a biological specimen collected from a swab. A reagent dispenser cap is removably mounted on the housing to permit placement of the specimen into the specimen chamber, at which time the dispenser cap may be manipulated to deliver one or more selected chemical reagents to the specimen chamber for contacting the collected specimen. A diagnostic strip assembly is also mounted on the housing and includes a diagnostic strip extending along the housing, substantially in parallel relative to the specimen chamber. Transfer means are provided for moving mixed specimen and reagent from the specimen chamber for contacting one end of the diagnostic strip and for wick flow therethrough into contact with one or more additional reagents selected to yield a visual test result.

However, one problem with conventional "all-in-one" systems, such as described above, is that the fluid contained within the apparatus often leaks out of the apparatus prior to use. In addition, the method for using such devices typically involves several complicated steps that may lower the real-time efficacy of the device in detecting the presence or absence of the analyte. As such a need currently exits for a self-contained, swab-based device that is effective in detecting the presence of an analyte in a simple manner.

SUMMARY OF THE INVENTION

In accordance with one embodiment of the present invention, a diagnostic test unit is disclosed. The test unit comprises a stem having a first end and a second end, the stem defining at least one flow channel extending between the first end and the second end. A swab is disposed at the first end of the stem, the swab being configured to collect a test sample derived from a biological source that is suspected of containing an analyte. The test unit also comprises a fluid chamber configured to contain a fluid, wherein the fluid chamber is in fluid communication with the swab via the flow channel. The test unit also comprises a rupturable seal that inhibits leakage of the fluid from the fluid chamber prior to use, and an assay for detecting the presence or absence of the analyte in the test sample. The assay is in fluid communication with the swab, the flow channel, and the fluid chamber.

In accordance with another embodiment of the present invention, a method for detecting the presence or absence of an analyte within a test sample derived from a biological source is disclosed. The method comprises:

i) providing a diagnostic test unit, the test unit comprising:

a) a stem having a first end and a second end, the stem defining at least one flow channel extending between the first end and the second end;
b) a swab disposed at the first end of the stem;
c) a fluid chamber configured to contain a fluid, wherein the fluid chamber is in fluid communication with the swab via the flow channel;
d) a seal that inhibits leakage of the fluid from the fluid chamber prior to use; and
e) an assay for detecting the presence or absence of the analyte in the test sample, the assay being in fluid communication with the swab, the flow channel, and the fluid chamber;

ii) collecting the test sample on the swab; and iii) rupturing the seal to release the fluid from the fluid chamber, wherein the fluid mixes with the test sample on the swab and then contacts the assay.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which:

FIG. 1 illustrates one embodiment of a diagnostic test unit of the present invention, in which FIG. 1A is a perspective view of the test unit and FIG. 1B is a cross-sectional view of the test unit;

FIG. 2 illustrates another embodiment of a diagnostic test unit of the present invention, in which

FIG. 3 illustrates another embodiment of a diagnostic test unit of the present invention, in which

FIG. 4 illustrates another embodiment of a diagnostic test unit of the present invention, in which FIG. 4A is a perspective view of the diagnostic test unit with first and second components shown separately and FIG. 4B is a cross-sectional view of the test unit with the first and second components shown inserted into a reader.

Figure 2A:
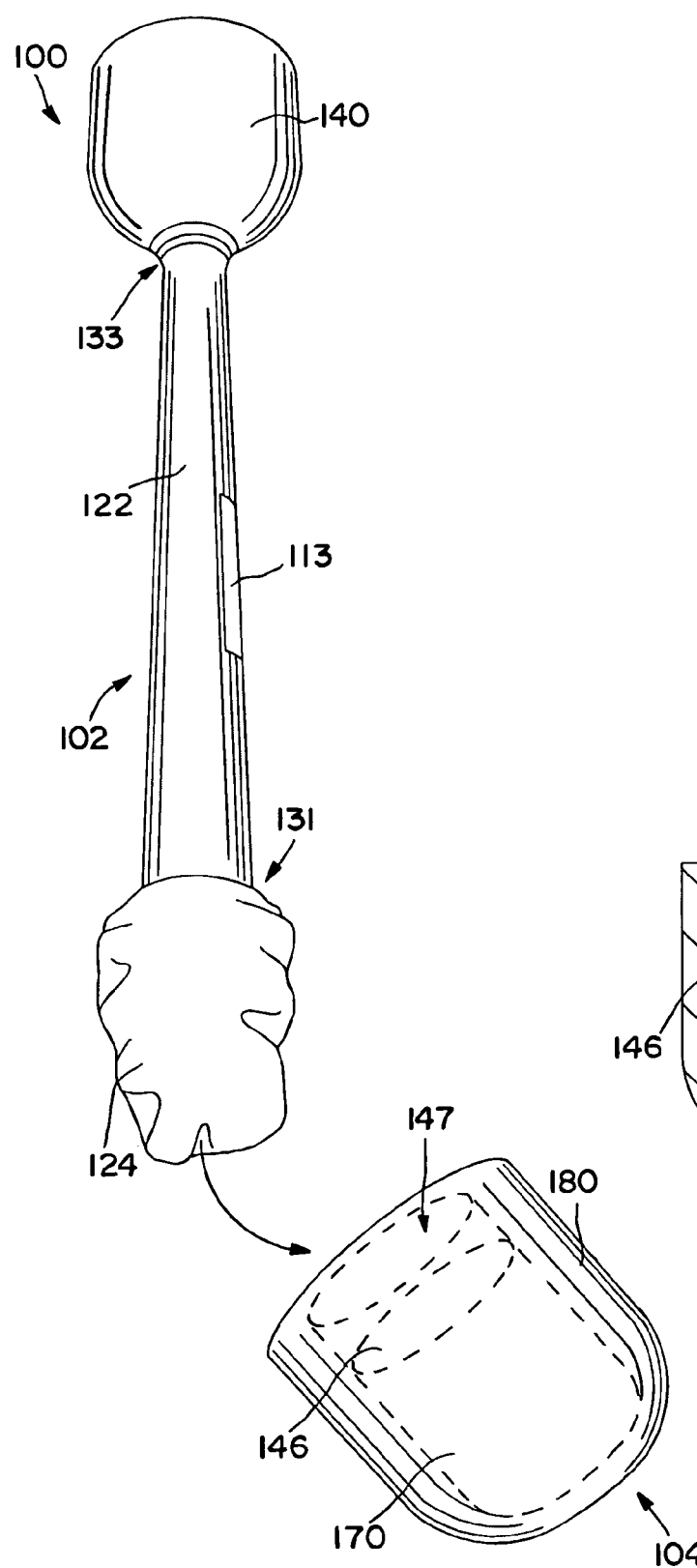
FIG. 2A is a perspective view of the diagnostic test unit with first and second components shown separately and FIG. 2B is a cross-sectional view of the test unit with the first component shown inserted into the second component.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "analyte" generally refers to a substance to be detected. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MB (CK-MB); digoxin; phenyloin; phenobarbitol; carbamazepine; vancomycin; gentamycin; theophylline; valproic acid; quinidine; luteinizing hormone (LH); follicle stimulating hormone (FSH); estradiol, progesterone; C-reactive protein; lipocalins; IgE antibodies; cytokines; vitamin B2 micro-globulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryoic antigen (CEA); lipoproteins, cholesterol, and triglycerides; and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. Nos. 6,436,651 to Everhart, et al. and 4,366,241 to Tom et al.

As used herein, the term "test sample" generally refers to a biological material suspected of containing the analyte. The test sample may be derived from any biological source, such as a physiological fluid, including, blood, interstitial fluid, saliva, ocular lens fluid, cerebral spinal fluid, sweat, urine, milk, ascites fluid, mucous, synovial fluid, peritoneal fluid, vaginal fluid, amniotic fluid, and so forth. Besides physiological fluids, other liquid samples may be used such as water, food products, and so forth, for the performance of environmental or food production assays. In addition, a solid material suspected of containing the analyte may be used as the test sample. The test sample may be used directly as obtained from the biological source or following a pretreatment to modify the character of the sample. For example, such pretreatment may include preparing plasma from blood, diluting viscous fluids, and the like. Methods of pretreatment may also involve filtration, precipitation, dilution, distillation, mixing, concentration, inactivation of interfering components, the addition of reagents, etc. Moreover, it may also be beneficial to modify a solid test sample to form a liquid medium or to release the analyte.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

In general, the present invention is directed to a diagnostic test unit is accurate, reliable, efficient, and easy to use. The test unit contains a swab for collecting a test sample suspected of containing an analyte of interest. As is well known in the art, the swab may be formed from a variety of different absorbent materials, such as cotton, rayon, pulp, etc., and may possess any desired shape and/or size. The swab is disposed at one end of a stem, which contains one or more flow channels. A fluid is contained within a fluid chamber that is in fluid communication with the flow channel(s). For example, the fluid may be a buffer fluid, such as phosphate-buffered saline (PBS) (e.g., pH of 7.2) or 2-(N-morpholino) ethane sulfonic acid (MES) (e.g., pH of 5.3). Other types of fluids or additives for the fluid may include detergents, salts, lysing agents (such as for detection of microbes, e.g., Strep bacteria or yeasts), blocking agents (e.g., bovine serum albumin), other proteins, and so forth. Still other optional materials that may be present within the fluid include labeled microparticles, detection probes, dyes, electrochemically-active agents (e.g., redox mediators), or other reagents used to create a signal for detection. The volume of the fluid contained within the fluid chamber is generally determined by the amount of reagent required for a particular test sample. Example volumes of the fluid are from about 50 to about 1000 microliters of fluid, with a typical amount being from about 100 to about 200 microliters.

In accordance with one aspect of the present invention, a user may controllably release the fluid from the fluid chamber after the test sample is collected on the swab. Various mechanisms may be employed to impart such selective control over the release of the fluid. For example, a seal may be used that is relatively resistant to diffusion of the fluid therethrough. The seal may be formed from a variety of different materials, such as nonporous films, metallic seals (e.g., aluminum foil), etc. Some suitable materials used in the fabrication of films for forming the seal may include thermoplastic polymers, such as polyolefins (e.g., polyethylene, polypropylene, etc.), including homopolymers, copolymers, terpolymers and blends thereof; ethylene vinyl acetate; ethylene ethyl acrylate; ethylene acrylic acid; ethylene methyl acrylate; ethylene normal butyl acrylate; polyurethane; poly(ether-ester); poly(amid-ether) block copolymers; and the like. Other suitable materials may include non-thermoplastic materials, silicone-based materials, other elastomeric materials, and so forth. In some embodiments, it is desired to minimize the thickness of the seal so that a user may easily rupture it. In such instances, the thickness of the seal may be less than about 0.05 inches, in some embodiments between about 0.0003 inches to about 0.01 inches, and in some embodiments, between about 0.0007 inches to about 0.02 inches.

Thus, prior to use, the seal may retain the fluid within the fluid chamber and inhibit leakage. To release the fluid and begin the diagnostic test, a user may simply rupture the seal. In some embodiments, once released, the fluid initially contacts the swab, mixes with the test sample, and then flows into the flow channel(s). Desirably, the flow channel(s) is of a sufficient length to allow an increased amount of time for the test sample and the fluid to mix before contacting an assay. In other embodiments, the fluid initially flows into the flow channel(s), and thereafter contacts the swab and mixes with the test sample. In either case, after contacting the swab and flowing into the flow channel(s), the resulting test sample/fluid mixture may then contact an assay for detecting the presence or absence of an analyte.

One or more of the components of the diagnostic test unit may be disposable and discarded after use. This reduces the likelihood of contamination after the performance of multiple tests, and thus enhances accuracy. Nevertheless, although one or more components of the diagnostic test unit may be disposable, the test unit may also include reusable components. For example, the disposable test unit may include a reader for quantitatively or qualitatively detecting the presence of an analyte. As is well known in the art, such a reader may utilize any of a variety of detection techniques. For example, the reader may utilize optical detection techniques (e.g., fluorescence, reflectance, densitometry, phosphorescence, diffraction, etc.); electrochemical detection techniques, and so forth. In one embodiment, a reflectance reader may be utilized to detect the presence of probes that exhibit a visual color (e.g. dyed latex microparticles). One suitable reflectance reader is described, for instance, in U.S. Patent App. Pub. No. 2003/0119202 to Kaylor, et al., which is incorporated herein in its entirety by reference thereto for all purposes. The reader may include a variety of optional components that benefit a user. For example, the reader may include a display (e.g., LED display) for providing digital or analog results to a user. The reader may also include one or more input devices (e.g., buttons or keys) that may be used, for instance, to facilitate data storage, allow connections to a computer or to the internet, etc. If desired, the reader may also function as a holder for other components of the test unit.

Regardless of the specific manner in which it is formed, one significant benefit of the diagnostic test unit of the present invention is that most, if not all of the components of the diagnostic test unit (e.g., swab, stem, flow channel(s), rupturable seal, assay, etc.), may be included within a single unit, i.e., they are "self-contained." Moreover, the self-contained test unit is also multi-functional. For example, the test unit is capable of accomplishing multiple tasks, such as blood filtration, cell lysing, carrying a label such as conjugate particles for the assay, etc. Further, the stem itself is multi-functional in that it is a support for the swab while also providing fluid/reagent transport to the swab. Such a self-contained, multi-functional test unit provides a number of benefits to a user, including simplicity, convenience, lower costs, enhanced safety, and so forth.

Of course, the present invention provides numerous other benefits as well. For example, the assay and/or reagents for the assay may be pre-supplied within the diagnostic test unit to reduce the likelihood of contamination prior to use, thereby improving accuracy and reliability. Another benefit of the present invention is that the swab may function as a filter of contaminants from the test sample and/or fluid before contacting the assay, thereby improving the accuracy and reliability of the diagnostic test.

Various embodiments of the diagnostic test unit of the present invention will now be described in more detail. It should be understood, however, that the embodiments discussed below are merely exemplary, and that any suitable configuration of the diagnostic test unit may also be utilized in the present invention. In this regard, referring to FIG. 1, one embodiment of a swab-based diagnostic test unit 10 that may be formed according to the present invention will now be described in more detail. As shown, the diagnostic test unit 10 includes a stem 22 having a first end 31 and a second end 33. A swab 24 is retained at the first end 31 of the stem 22. A base portion 40 is also disposed at the second end 33 of the stem 22. The base portion 40 may be formed integral with or separate from the stem 22. For example, in one embodiment, the stem 22 is removable from the base portion 40 by a user. In this manner, a user may remove the stem 22 and the swab 24 when it is desired to collect a test sample, and then re-position the stem 22 over the base portion 40 when it is desired to initiate the diagnostic test. The stem 22 and the base portion 40 may be made from any of a variety of materials, such as molded or blown plastic.

The stem 22 and the base portion 40 may have a shape to enable easy manual handling during use. For instance, the stem 22 may be generally elongated and tubular, while the base portion 40 has a substantially conical shape. As will be described in more detail below, the generally elongated shape of the stem 22 may facilitate mixing of the test sample and a fluid, and also facilitate sampling with the swab 24. In addition, the "curved" shape of the base portion 40 may facilitate gripping of the diagnostic test unit 10 by a user. It should be understood that the shapes and/or sizes described above are merely exemplary, and that virtually any shape and/or size may be used to form the stem 22 and the base portion 40. For instance, other examples of suitable shapes for the stem 22 and/or the base portion 40 include, but are not limited to, square, rectangular, triangular, circular, oval, trapezoidal, elliptical, parabolic, irregular shapes, and so forth.

The base portion 40 defines a chamber 70 within which a fluid is provided for mixing with a test sample collected on the swab 24. The chamber 70 is in fluid communication with the swab 24 disposed on the stem 22. In the illustrated embodiment, for instance, the stem 22 defines a first flow channel 50 extending between the first end 31 and the second end 33 so that the fluid is capable of flowing from the base portion 40 into the first channel 50, and then to the swab 24, as exemplified by the directional arrows shown in FIG. 1B. The size and/or surface energy of the first channel 50 may be selected to facilitate mixing between the test sample and fluid, and so that capillary forces facilitate the flow of the fluid from the base portion 40 to the swab 24. For example, the length of the first channel 50 may be greater than about 1 centimeter, in some embodiments from about 1 to about 15 centimeters, and in some embodiments, from about 5 to about 10 centimeters. The width (or diameter) of the first channel 50 may be substantially constant, or may alternatively vary as a function of length. For instance, in the embodiment illustrated in FIG. 1, the width of the first channel 50 decreases gradually from the first end 31 to the second end 33. Regardless, the width of at least a portion of the first channel 50 is typically less than about 3 millimeters, in some embodiments from about 0.01 to about 3 millimeters, and in some embodiments, from about 0.05 to 1 millimeter.

After contacting the swab 24, the fluid mixes with the test sample collected by the user and then flows through a second flow channel 52, where it contacts an assay 60 (FIG. 1B). The second channel 52 may have the same or different size and shape as the first channel 50. Of course, a small portion of the fluid and test sample may also flow back through the first channel 50 without contacting the assay 60. Without intending to be limited by theory, however, it is believed that the capillary forces imparted by the dimensions of the first channel 50 will ultimately force most, if not all of the mixture, through the second channel 52. It should also be understood that the use of two channels is merely exemplary, and that any number of channels may be utilized in the present invention. For example, as will be described in more detail below, a single flow channel may be utilized in some embodiments of the present invention.

As shown, a seal 46 may also be positioned between the first channel 50 and the fluid within the chamber 70 that is relatively resistant to diffusion of the fluid therethrough. To release the fluid from the chamber 70 and into the first channel 50, the user may, in one embodiment, depress a button 44 or any other activation device to rupture the seal 46 and release the fluid. Specifically, the button 44 is connected to a moveable pin 48 that is placed into contact with the seal 46 upon depression of the button 44. Thus, when depressed, the pin 48 moves in a vertical direction until it contacts the seal 46 and is inserted therethrough. Once the seal 46 is ruptured, the fluid is released from the chamber 70.

Figure 2B:
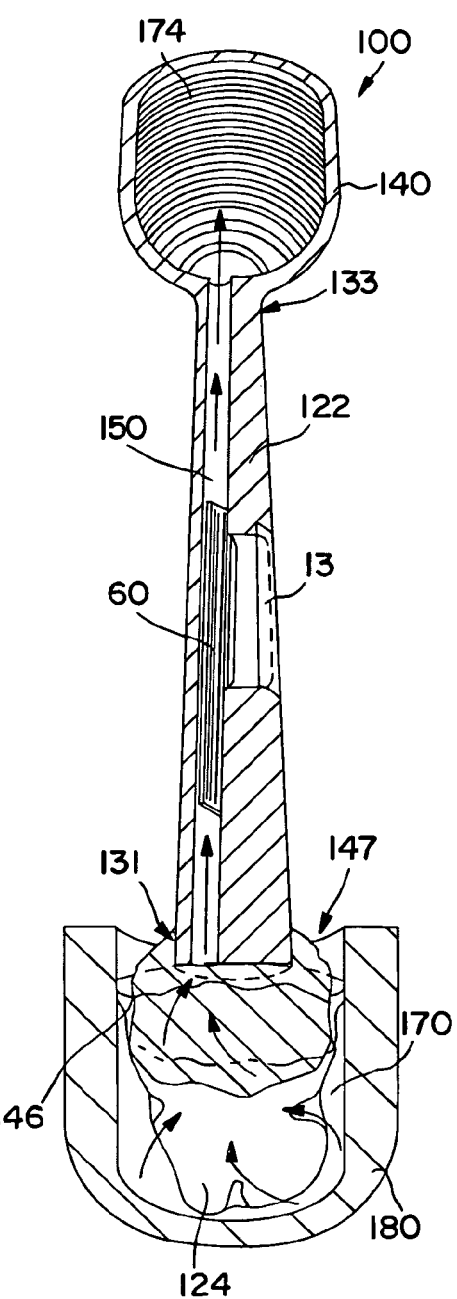

Referring to FIG. 2, another embodiment of a swab-based diagnostic test unit 100 that may be formed according to the present invention is shown. In this embodiment, the diagnostic test unit 100 includes two components, i.e., a first component 102 and a second component 104. Similar to the embodiment shown in FIG. 1, the first component 102 includes a stem 122 having a first end 131 and a second end 133. A swab 124 is retained at the first end 131 of the stem 122. In addition, a base portion 140 is also disposed at the second end 133 of the stem 122. The second component 104 has an outer wall 180 that defines a fluid chamber 170 within which a fluid is retained. Prior to use, a seal 146 inhibits leakage of the fluid from the chamber 170. Once the test sample is collected, the first component 102 may be inserted into the second component 104 to initiate the diagnostic test. Specifically, a user may insert the swab 124 into an opening 147 of the second component 104 until the swab 124 contacts the seal 146 and causes it to rupture. Alternatively, the seal 146 may be ruptured in various other ways, such as by squeezing the outer wall 180 of the second component 104 with a sufficient force to cause the seal 146 to rupture. If desired, various sealing mechanisms may be utilized to ensure that a substantial amount of fluid does not leak from the opening 147 after insertion of the swab 124. For example, a hydraulic seal, such as o-rings, t-rings, d-rings, v-rings, etc., may be utilized. As is well known in the art, such hydraulic seals would provide a sealing fit between the outer surface of the stem 122 and the inner surface of the opening 147.

After rupturing the seal 146, the fluid is released from the chamber 170 and contacts the swab 124. The fluid then flows through the swab 124 and into a flow channel 150, where it contacts an assay 60 for detecting the presence of an analyte within the test sample. The dimensions of the flow channel 150 may, as described above, be sufficient to facilitate mixing of the test sample and fluid, as well as to promote capillary flow. Apart from the capillary forces associated with the dimensions of the flow channel 150, an absorbent pad 174 contained within the base portion 140 may also assist in promoting capillary action and fluid flow through the channel 150. For example, the absorbent pad 174 may be formed from a cellulosic-based material.

Another embodiment of a diagnostic test unit 300 that may be used in the present invention is shown in FIG. 4. The embodiment shown in FIG. 4 functions in a manner similar to FIG. 2, without the use of the base portion 140 (FIG. 2). Specifically, the diagnostic test unit 300 includes two components, i.e., a first component 302 and a second component 304. Similar to the embodiment shown in FIG. 1, the first component 302 includes a stem 322 having a first end 331 and a second end 333. A swab 324 is retained at the first end 331 of the stem 322. The second component 304 has an outer wall 380 that defines a fluid chamber 370 within which a fluid is retained. Prior to use, a seal 346 inhibits leakage of the fluid from the chamber 370. Once the test sample is collected, the first component 302 may be inserted into the second component 304 to initiate the diagnostic test. Specifically, a user may insert the swab 324 into an opening 347 of the second component 304 until the swab 324 contacts the seal 346 and causes it to rupture. After rupturing the seal 346, the fluid is released from the chamber 370 and contacts the swab 324. The fluid then flows through the swab and into a flow channel 350, where it contacts an assay 60 for detecting the presence of an analyte within the test sample.

If desired, both the first component 302 and the second component 304 may be placed into a reader 390 for analyzing the results of the assay. As shown in FIG. 4B, for instance, the end 333 of the stem 322 may be inserted through an opening 391 of the reader 390. The first component 302 may be placed over the second component 304, as described above, either before or after insertion of the stem 322 into the reader 390. The reader 390 may include a variety of optional components that benefit a user. For example, the reader 390 may include a display 395 (e.g., LED display) for providing digital or analog results to a user. The reader 390 may also include one or more buttons 393 that may be used, for instance, to facilitate data storage, to allow connections to a computer or to the internet, etc. In some cases, the reader 390 may be reusable for other diagnostic tests, while the remaining components of the test unit 300 may be disposable. Moreover, in some embodiments, the assay 60 may also be contained within the reader 390. This may provide a number of benefits, such as allowing the assay 60 to be washed with a liquid supplied by a separate rinsing reservoir (not shown) present within the reader 390.

Referring to FIG. 3, still another embodiment of a swab-based diagnostic test unit 200 that may be formed according to the present invention is shown. Similar to the embodiment shown in FIG. 2, the diagnostic test unit 200 includes two components, i.e., a first component 202 and a second component 204. As described above, the first component 202 includes a stem 222 having a first end 231 and a second end 233. A swab 224 is retained at the first end 231 of the stem 222. In this embodiment, a syringe 240 is also disposed at the second end 233 of the stem 222. The syringe 240 includes a housing 245 that defines an opening 249 through which a moveable shaft 242 is inserted. The housing 245 also defines a fluid chamber 270 within which a fluid is retained. Prior to collection of the test sample, the fluid remains sealed within the chamber 270 between a base 244 of the shaft 242 and a seal 246. As described in more detail above, the seal 246 is liquid-impermeable and inhibits premature leakage of the fluid into a channel 250 of the stem 222.

Figure 3A:
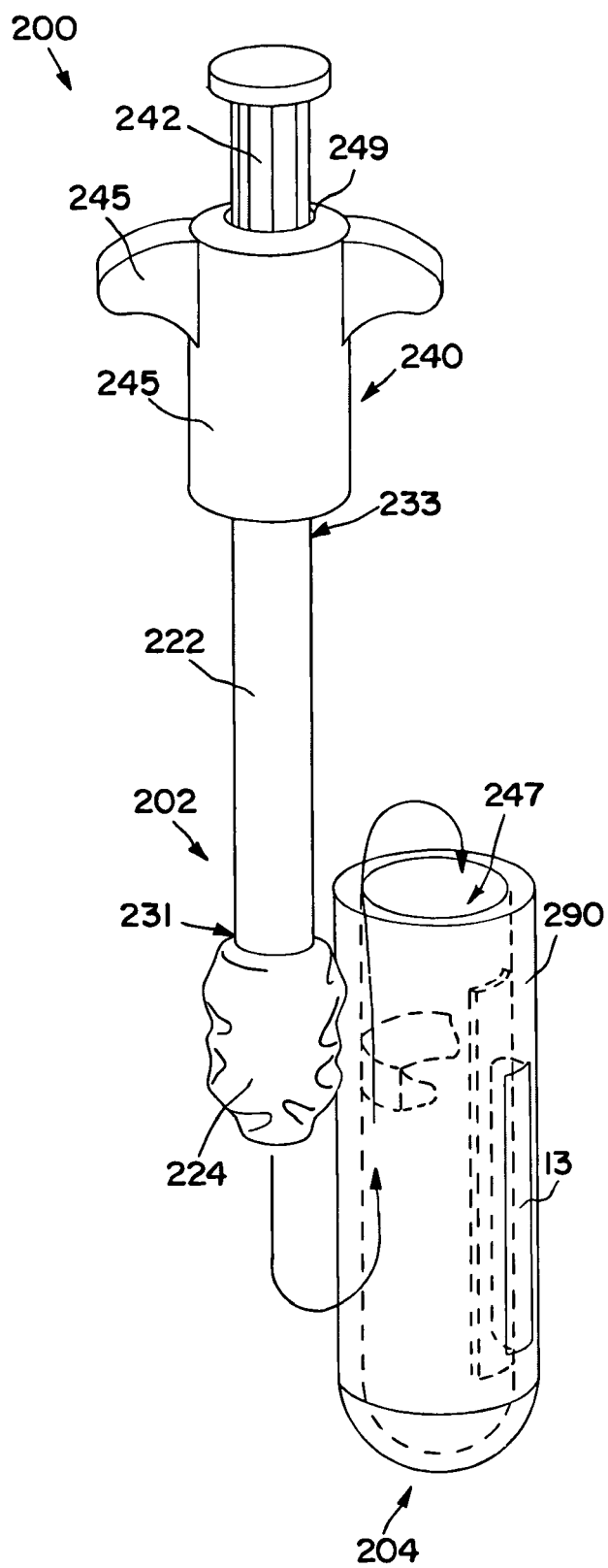
FIG. 3A is a perspective view of the diagnostic test unit with first and second components shown separately and FIG. 3B is a cross-sectional view of the test unit with the first component shown inserted into the second component.

As indicated by the directional arrows of FIG. 3A, a user may insert the swab 224 into a detection chamber 247 defined by an outer wall 290 of the second component 204 after collecting the test sample. The size and shape of the detection chamber 247 may be selected to correspond to the size and shape of the swab 224 and/or stem 222. If desired, a lip 271 may be positioned within the detection chamber 247 to prevent over-insertion of the shaft 222. Namely, the lip 271 prevents the swab 224 from being positioned so far below the assay 60 that the diagnostic test might be ineffective. Other than the lip 271, various other stopping mechanisms may also be used. For instance, in one embodiment, the width (or diameter) of a portion of the shaft 222 may simply be larger than the width (or diameter) of the opening 247, thus inhibiting over-insertion. As mentioned above, hydraulic seal mechanisms may also be utilized to inhibit the leakage of fluid through the detection chamber 247 after insertion of the swab 224.

Figure 3B:
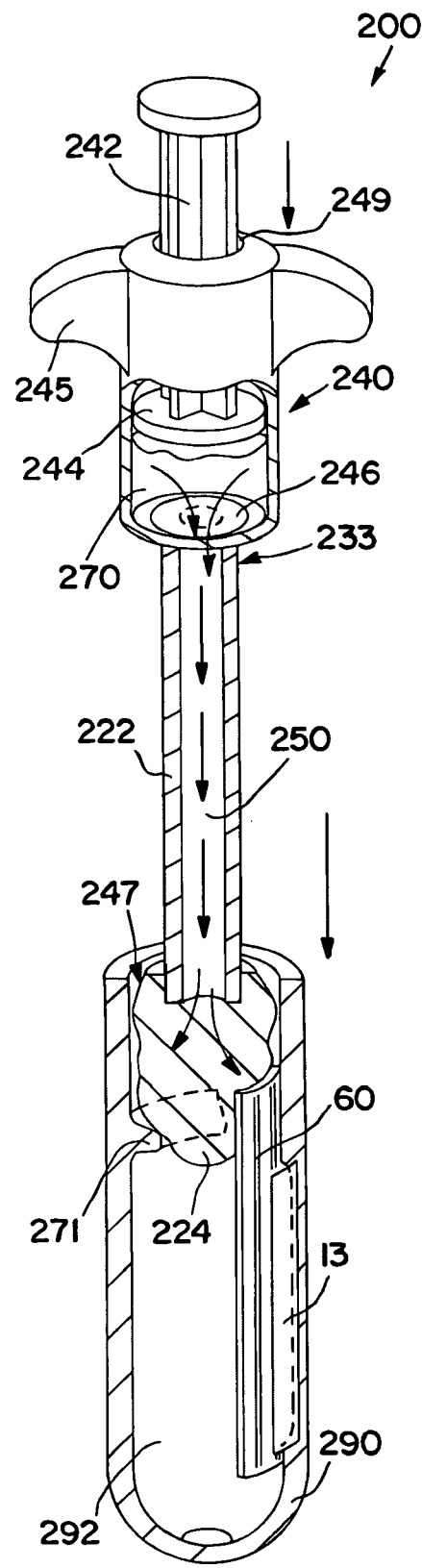

Upon insertion of the swab 224 into the detection chamber 247, a user may activate the diagnostic test by depressing the shaft 242 as shown by the directional arrow of FIG. 3B. Depression of the shaft 242 causes the fluid pressure within the fluid chamber 270 to increase until the seal 246 is ruptured. The rupture of the seal 246 allows the fluid to flow from the chamber 270 into a flow channel 250 within the stem 222. The fluid flows through the channel 250 and mixes with the test sample present on the swab 224. Thereafter, the mixture of the fluid and test sample may contact an assay 60 (e.g., test strip) for detecting the presence of an analyte within the test sample.

Figure 5:
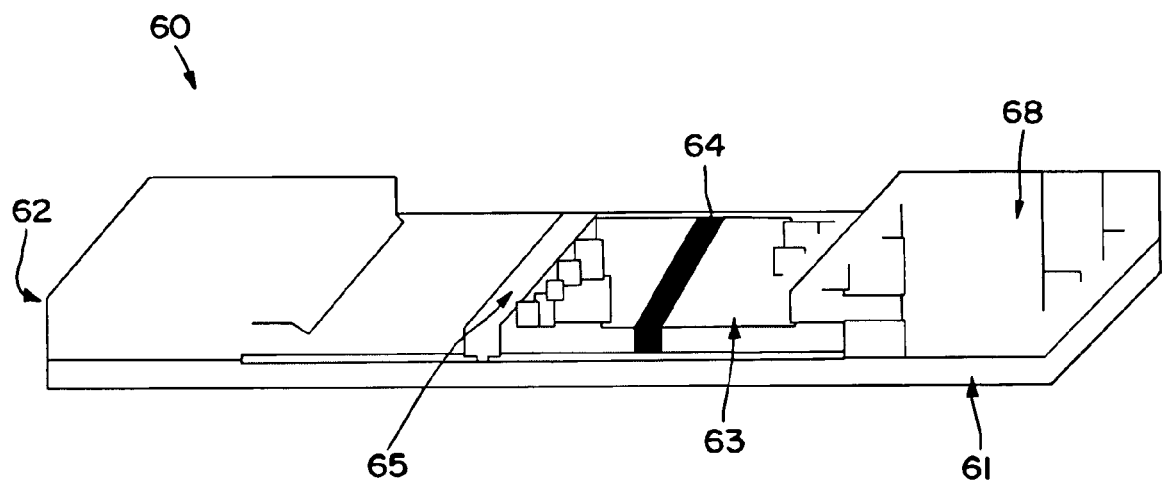
FIG. 5 is a perspective view of an assay that may be utilized in one embodiment of the present invention.

For purposes of illustration only, various examples of the assay 60 of FIGS. 1–4 will now be described in more detail. It should be understood, however, that other assays are also contemplated by the present invention. In fact, the present invention is not limited to any particular assay configuration. In this regard, referring to FIG. 5, one embodiment of an assay 60 is illustrated that is a lateral flow test strip that performs an immunoassay. Immunoassays utilize mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that may be used to determine the presence or concentration of that particular antigen in a test sample.

In the illustrated embodiment, the assay 60 contains a porous membrane 63 optionally supported by a rigid material 61. In general, the porous membrane 63 may be made from any of a variety of materials through which a fluid is capable of passing. For example, the materials used to form the porous membrane 63 may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and the like. In one particular embodiment, the porous membrane 463 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The assay 60 may also contain an absorbent pad 68. The absorbent pad 68 generally receives fluid that has migrated through the entire porous membrane 63. As is well known in the art, the absorbent pad 68 may assist in promoting capillary action and fluid flow through the membrane 63. Some suitable materials that may be used to form the sample pad include, but are not limited to, nitrocellulose, cellulose, porous polyethylene pads, and glass fiber filter paper. If desired, the sample pad may also contain one or more assay pretreatment reagents, either covalently or non-covalently attached thereto. In the illustrated embodiment, the test sample travels from the sample pad (not shown) to a conjugate pad 62 that is placed in communication with one end of the sampling pad. The conjugate pad 62 is formed from a material through which a fluid is capable of passing. For example, in one embodiment, the conjugate pad 62 is formed from glass fibers. Although only one conjugate pad 62 is shown, it should be understood that other conjugate pads may also be used in the present invention.

To facilitate detection of the presence or absence of an analyte within the test sample, various detection probes may be applied to the conjugate pad 62. While contained on the conjugate pad 62, these detection probes remain available for binding with the analyte as it passes from the sampling pad through the conjugate pad 62 (or optionally in the fluid). Upon binding with the analyte, the detection probes may later serve to identify the presence or absence of the analyte. The detection probes may be used for both detection and calibration of the assay 60. In alternative embodiments, however, separate calibration probes may be applied to the conjugate pad 62 for use in conjunction with the detection probes to facilitate simultaneous calibration and detection, thereby eliminating inaccuracies often created by conventional assay calibration systems. It should be understood, however, that the detection probes and/or the calibration probes may be applied together or separately at any location of the assay 60, and need not be applied to the conjugate pad 62. Further, it should also be understood that the detection probes and/or the calibration probes may be applied to the same or different conjugate pads. Alternatively, the detection probes and/or calibration probes may be located in a separate area of the diagnostic test unit 10, 100, 200, or 300 (FIGS. 1–4), such as within the fluid, flow channel, or swab.

In some instances, it may be desired to modify the detection probes in some manner so that they are more readily able to bind to the analyte. In such instances, the detection probes may be modified with certain specific binding members that are adhered thereto to form conjugated probes. Specific binding members generally refer to a member of a specific binding pair, i.e., two different molecules where one of the molecules chemically and/or physically binds to the second molecule. For instance, immunoreactive specific binding members may include antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin (or derivatives thereof), biotin and streptavidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte, i.e., an analyte-analog, may be used so long as it has at least one epitope in common with the analyte.

The specific binding members may generally be attached to the detection probes using any of a variety of well-known techniques. For instance, covalent attachment of the specific binding members to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer because the surface of the detection probe may contain a relatively high surface concentration of polar groups. In addition, although detection probes are often functionalized after synthesis, in certain cases, such as poly(thiophenol), the probes are capable of direct covalent linking with a protein without the need for further modification. Besides covalent bonding, other attachment techniques, such as physical adsorption, may also be utilized.

In one embodiment, for instance, the fluid containing the test sample travels to the conjugate pad 62, where the analyte mixes with detection probes modified with a specific binding member to form analyte complexes. Because the conjugate pad 62 is in fluid communication with the porous membrane 63, the complexes may migrate from the conjugate pad 62 to a detection zone 65 present on the porous membrane 63. The detection zone 65 may contain an immobilized receptive material that is generally capable of forming a chemical or physical bond with the analyte and/or complexes thereof (e.g., complexes of the analyte with the detection probes). In some embodiments, the receptive material may be a biological receptive material. Such biological receptive materials are well known in the art and may include, but are not limited to, antigens, haptens, antibodies, protein A or G, avidin, streptavidin, and complexes thereof. In some cases, it is desired that these biological receptive materials are capable of binding to the analyte and/or the complexes of the analyte with the detection probes.

These receptive materials serve as stationary binding sites for the detection probe/analyte complexes. In some instances, the analytes, such as antibodies, antigens, etc., have two binding sites. Upon reaching the detection zone 65, one of these binding sites is occupied by the specific binding member of the complexed probes. However, the free binding site of the analyte may bind to the immobilized receptive material. Upon being bound to the immobilized receptive material, the complexed probes form a new ternary sandwich complex.

The detection zone 65 may generally provide any number of distinct detection regions so that a user may better determine the concentration of a particular analyte within a test sample. Each region may contain the same receptive materials, or may contain different receptive materials for capturing multiple analytes. For example, the detection zone 65 may include two or more distinct detection regions (e.g., lines, dots, etc.). The detection regions may be disposed in the form of lines in a direction that is substantially perpendicular to the flow of the test sample through the assay 60. Likewise, in some embodiments, the detection regions may be disposed in the form of lines in a direction that is substantially parallel to the flow of the test sample through the assay device.

Although the detection zone 65 may indicate the presence of an analyte, it is often difficult to determine the relative concentration of the analyte within the test sample using solely a detection zone 65. Thus, the assay 60 may also include a calibration zone 64. In this embodiment, the calibration zone 64 is formed on the porous membrane 63 and is positioned downstream from the detection zone 65. The calibration zone 64 is provided with a receptive material that is capable of binding to any remaining uncaptured detection probes and/or calibration probes that pass through the length of the membrane 63. In particular, upon being contacted with the test sample, any uncaptured probes that do not bind to the analyte migrate through the detection zone 65 and enter the calibration zone 64 of the porous membrane 63. At the calibration zone 64, these uncaptured probes then bind to the receptive materials.

The receptive materials utilized in the calibration zone 64 may be the same or different than the receptive materials used in the detection zone 65. For instance, in some embodiments, the receptive material may include a polyelectrolyte that may bind to the uncaptured probes. The polyelectrolytes may have a net positive or negative charge, as well as a net charge that is generally neutral. For instance, some suitable examples of polyelectrolytes having a net positive charge include, but are not limited to, polylysine (commercially available from Sigma-Aldrich Chemical Co., Inc. of St. Louis, Mo.), polyethylenimine; epichlorohydrin-functionalized polyamines and/or polyamidoamines, such as poly(dimethylamine-co-epichlorohydrin); polydiallyldimethylammonium chloride; cationic cellulose derivatives, such as cellulose copolymers or cellulose derivatives grafted with a quaternary ammonium water-soluble monomer; and the like. In one particular embodiment, CelQuat® SC-230M or H-100 (available from National Starch & Chemical, Inc.), which are cellulosic derivatives containing a quaternary ammonium water-soluble monomer, may be utilized. Moreover, some suitable examples of polyelectrolytes having a net negative charge include, but are not limited to, polyacrylic acids, such as poly(ethylene-co-methacrylic acid, sodium salt), and the like. It should also be understood that other polyelectrolytes may also be utilized in the present invention, such as amphiphilic polyelectrolytes (i.e., having polar and non-polar portions). For instance, some examples of suitable amphiphilic polyelectrolytes include, but are not limited to, poly(styryl-b-N-methyl 2-vinyl pyridinium iodide) and poly(styryl-b-acrylic acid), both of which are available from Polymer Source, Inc. of Dorval, Canada.

Similar to the detection zone 65, the calibration zone 64 may also provide any number of distinct calibration regions in any direction so that a user may better determine the concentration of a particular analyte within a test sample. The calibration regions may be pre-loaded on the porous membrane 63 with different amounts of the binder so that a different signal intensity is generated by each calibration region upon migration of the uncaptured probes. The overall amount of receptive material within each calibration region may be varied by utilizing calibration regions of different sizes and/or by varying the concentration or volume of the binder in each calibration region. If desired, an excess of probe molecules may be employed in the assay 60 so that each calibration region reaches its full and predetermined potential for signal intensity. That is, the amount of uncaptured probes that are deposited upon calibration regions are predetermined because the amount of the binder employed on the calibration regions is set at a predetermined and known level. Once captured, the signal of the probes at the detection and calibration zones 65 and 64 may be measured visually or through other methods of detection (e.g., instruments). When determined visually, the diagnostic test unit 10, 100, 200, or 300 may optionally be provided with a window 13 (FIGS. 1–4) as is well known in the art so that a user may readily observe the assay 60.

In some cases, the membrane 63 may also define a control zone (not shown) that gives a signal to the user that the assay is performing properly. For instance, the control zone (not shown) may contain an immobilized receptive material that is generally capable of forming a chemical and/or physical bond with probes or with the receptive material immobilized on the probes. Some examples of such receptive materials include, but are not limited to, antigens, haptens, antibodies, protein A or G, avidin, streptavidin, secondary antibodies, and complexes thereof. In addition, it may also be desired to utilize various non-biological materials for the control zone receptive material. For instance, in some embodiments, the control zone receptive material may also include a polyelectrolyte, such as described above, that may bind to uncaptured probes. Because the receptive material at the control zone is only specific for probes, a signal forms regardless of whether the analyte is present. The control zone may be positioned at any location along the membrane 63, but is preferably positioned upstream from the detection zone 65.

Various formats may be used to test for the presence or absence of an analyte using the assay 60. For instance, in the embodiment described above, a "sandwich" format is utilized. Other examples of such sandwich-type assays are described by U.S. Pat. Nos. 4,168,146 to Grubb, et al. and 4,366,241 to Tom, et al., which are incorporated herein in their entirety by reference thereto for all purposes. In addition, other formats, such as "competitive" formats, may also be utilized. In a competitive assay, the labeled probe is generally conjugated with a molecule that is identical to, or an analogue of, the analyte. Thus, the labeled probe competes with the analyte of interest for the available receptive material. Competitive assays are typically used for detection of analytes such as haptens, each hapten being monovalent and capable of binding only one antibody molecule. Examples of competitive immunoassay devices are described in U.S. Pat. Nos. 4,235,601 to Deutsch, et al., 4,442,204 to Liotta, and 5,208,535 to Buechler, et al., which are incorporated herein in their entirety by reference thereto for all purposes. Various other device configurations and/or assay formats are also described in 5,395,754 to Lambofte, et al.; U.S. Pat. No. 5,670,381 to Jou, et al.; and 6,194,220 to Malick, et al., which are incorporated herein in their entirety by reference thereto for all purposes.

In addition, it should be understood that any known detection technique may be utilized in the present invention. For example, as is well known in the art, the assay 60 may also be an electrochemical affinity assay, which detects an electrochemical reaction between an analyte (or complex thereof) and a capture ligand on an electrode strip. For example, various electrochemical assays are described in U.S. Pat. Nos. 5,508,171 to Wallinq, et al.; 5,534,132 to Vreeke, et al.; 6,241,863 to Monbouquette; 6,270,637 to Crismore, et al.; 6,281,006 to Heller, et al.; and 6,461,496 to Feldman, et al., which are incorporated herein in their entirety by reference thereto for all purposes.

It has been discovered that the system of the present invention provides a relatively simple, compact and cost-efficient device for facilitated collecting and substantially immediate on-site testing of analytes. The system enables quick and easy specimen collection with a swab. Thereafter, the test unit may be manipulated to analyze the collected specimen and provide a test result. The test result may be visible so that it is readily observed by the person performing the test in a prompt manner and under test conditions conducive to highly reliable and consistent test results. After initial specimen collection, human contact with the specimen is thus substantially precluded throughout the test protocol, and the entire portion of the device with the collected specimen safely contained therein may be discarded as a unit when the test is concluded.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A diagnostic test unit comprising:
    a stem having a first end and a second end, said stem defining at least one flow channel extending between said first end and said second end;
    a swab disposed at said first end of said stem, said swab being configured to collect a test sample derived from a biological source that is suspected of containing an analyte;
    a fluid chamber configured to contain a fluid, wherein said fluid chamber is in fluid communication with said swab via said flow channel;
    a rupturable seal that inhibits leakage of the fluid from said fluid chamber prior to use; and
    a test strip for detecting the presence or absence of the analyte in the test sample, said test strip being in fluid communication with said swab, said flow channel, and said fluid chamber.

2. A diagnostic test unit as defined in claim 1, wherein said flow channel has a length of greater than about 1 centimeter.

3. A diagnostic test unit as defined in claim 1, wherein said flow channel has a length of from about 5 to about 10 centimeters.

4. A diagnostic test unit as defined in claim 1, wherein at least a portion of said flow channel has a width of less than about 3 millimeters.

5. A diagnostic test unit as defined in claim 1, wherein at least a portion of said flow channel has a width of from about 0.05 to about 1 millimeter.

6. A diagnostic test unit as defined in claim 1, further comprising a base portion disposed at said second end of said stem.

7. A diagnostic test unit as defined in claim 6, wherein said base portion defines said fluid chamber.

8. A diagnostic test unit as defined in claim 6, wherein said base portion includes an absorbent pad to facilitate wicking.

9. A diagnostic test unit as defined in claim 1, further comprising a syringe disposed at said second end of said stem.

10. A diagnostic test unit as defined in claim 9, wherein said syringe defines said fluid chamber.

11. A diagnostic test unit as defined in claim 1, wherein said fluid chamber is defined by a component configured to selectively receive said swab.

12. A diagnostic test unit as defined in claim 11, wherein said seal is configured to be ruptured by said swab when received by said component.

13. A diagnostic test unit as defined in claim 1, wherein said stem defines at least one additional flow channel.

14. A diagnostic test unit as defined in claim 13, wherein the fluid is capable of flowing from said fluid chamber through one of said flow channels to contact said swab, and the fluid is capable of flowing from said swab through another of said flow channels to contact said test strip.

15. A diagnostic test unit as defined in claim 1, wherein said test strip is positioned within said flow channel.

16. A diagnostic test unit as defined in claim 1, wherein said seal is formed from film, metallic foil, or combinations thereof.

17. A diagnostic test unit as defined in claim 1, wherein said seal has a thickness of less than about 0.05 inches.

18. A diagnostic test unit as defined in claim 1, wherein said seal has a thickness of from about 0.0007 inches to about 0.02 inches.

19. A diagnostic test unit as defined in claim 1, wherein the fluid is configured to flow from said fluid chamber, into said flow channel, and then contact said swab.

20. A diagnostic test unit as defined in claim 1, wherein the fluid is configured to flow from said fluid chamber, contact said swab, and then flow into said flow channel.

21. A diagnostic test unit as defined in claim 1, wherein said test strip comprises a porous membrane through which said fluid is capable of flowing.

22. A diagnostic test unit as defined in claim 1, further comprising a reader capable of detecting the presence of the analyte on said test strip.

23. A diagnostic test unit as defined in claim 1, wherein said test strip contains an immunoreactant.

24. A diagnostic test unit comprising:
   a generally elongated, tubular stem having a first end and a second end, said stem defining at least one flow channel extending between said first end and said second end, said flow channel having a length of from about 1 to about 15 centimeters and at least a portion of said flow channel having a width of from about 0.01 to about 3 millimeters;
   a swab disposed at said first end of said stem, said swab being configured to collect a test sample derived from a biological source that is suspected of containing an analyte;
   a fluid chamber configured to contain a fluid, wherein said fluid chamber is in fluid communication with said swab via said flow channel;
   a rupturable seal that inhibits leakage of the fluid from said fluid chamber prior to use, wherein said seal is formed from film, metallic foil, or combinations thereof, and has a thickness of less than about 0.05 inches; and
   a test strip for detecting the presence or absence of the analyte in the test sample, said test strip comprising a porous membrane that is in fluid communication with said swab, said flow channel, and said fluid chamber.

25. A diagnostic test unit as defined in claim 24, further comprising a base portion disposed at said second end of said stem.

26. A diagnostic test unit as defined in claim 25, wherein said base portion defines said fluid chamber.

27. A diagnostic test unit as defined in claim 25, wherein said base portion includes an absorbent pad to facilitate wicking.

28. A diagnostic test unit as defined in claim 24, further comprising a syringe disposed at said second end of said stem.

29. A diagnostic test unit as defined in claim 28, wherein said syringe defines said fluid chamber.

30. A diagnostic test unit as defined in claim 24, wherein said fluid chamber is defined by a component configured to selectively receive said swab.

31. A diagnostic test unit as defined in claim 30, wherein said seal is configured to be ruptured by said swab when received by said component.

32. A diagnostic test unit as defined in claim 24, wherein said stem defines at least one additional flow channel.

33. A diagnostic test unit as defined in claim 32, wherein the fluid is capable of flowing from said fluid chamber through one of said flow channels to contact said swab, and the fluid is capable of flowing from said swab through another of said flow channels to contact said test strip.

34. A diagnostic test unit as defined in claim 24, wherein said test strip is positioned within said flow channel.

35. A method for detecting the presence or absence or amount of an analyte within a test sample derived from a biological source, said method comprising:
   i) providing a diagnostic test unit, said test unit comprising:
      a) a stem having a first end and a second end, said stem defining at least one flow channel extending between said first end and said second end;
      b) a swab disposed at said first end of said stem;
      c) a fluid chamber configured to contain a fluid, wherein said fluid chamber is in fluid communication with said swab via said flow channel;
      d) a seal that inhibits leakage of the fluid from said fluid chamber prior to use; and
      e) a test strip for detecting the presence or absence of the analyte in the test sample, said test strip being in fluid communication with said swab, said flow channel, and said fluid chamber;
   ii) collecting the test sample on said swab;
   iii) rupturing said seal to release said fluid from said fluid chamber, wherein said fluid mixes with the test sample on said swab and then contacts said test strip and generates a detection signal; and
   iv) further comprising correlating the detection signal to the presence or amount of the analyte.

36. A method as defined in claim 35, wherein said flow channel has a length of greater than about 1 centimeter.

37. A method as defined in claim 35, wherein at least a portion of said flow channel has a width of from about 0.01 to about 3 millimeters.

38. A method as defined in claim 35, wherein said seal is ruptured by physically puncturing said seal.

39. A method as defined in claim 38, wherein seal is ruptured by inserting said swab through said seal.

40. A method as defined in claim 35, wherein said seal is ruptured by fluid pressure.

41. A method as defined in claim 40, wherein said seal is ruptured by depressing a shaft of a syringe.

42. A method as defined in claim 35, wherein said test strip is positioned within said flow channel.

43. A method as defined in claim 35, wherein said rupturing of said seal causes said fluid to flow from said fluid chamber, into said flow channel, and then contact said swab.

44. A method as defined in claim 35, wherein said rupturing of said seal causes said fluid to flow from said fluid chamber, contact said swab, and then flow into said flow channel.

45. A method as defined in claim 35, wherein said test strip contains an immunoreactant.

46. A method as defined in claim 35, further comprising calibrating said detection signal with a calibration signal generated by said test strip, wherein the amount of the analyte within the test sample is determined from said detection signal as calibrated by said calibration signal.

* * * * *